United States Patent [19]

Koeneman

[11] 4,231,122

[45] Nov. 4, 1980

[54] KNEE JOINT PROSTHESIS

[75] Inventor: James B. Koeneman, Erie, Pa.

[73] Assignee: Lord Corporation, Erie, Pa.

[21] Appl. No.: 852,111

[22] Filed: Nov. 16, 1977

[51] Int. Cl.$^3$ .............................................. A61F 1/03
[52] U.S. Cl. ........................................ 3/1.911; 3/22
[58] Field of Search ................... 3/1.91, 1.911, 1.912, 3/1.913, 17 R, 18, 22, 29, 30, 31, 32, 12, 12.2, 12.4; 403/224, 120, 225, 228

[56] References Cited

U.S. PATENT DOCUMENTS

| 708,685 | 9/1902 | White | 3/31 X |
|---|---|---|---|
| 2,183,076 | 12/1939 | Kaiser | 3/6 |
| 2,692,392 | 10/1954 | Bennington et al. | 3/33 |
| 3,480,972 | 12/1969 | Prahl | 3/33 |
| 3,707,006 | 12/1972 | Bokros et al. | 3/1 |
| 3,875,594 | 4/1975 | Swanson | 3/1 |
| 3,909,854 | 10/1975 | Martinez | 3/1.911 |
| 3,916,451 | 11/1975 | Buechel et al. | 3/1.91 |
| 4,034,418 | 7/1977 | Jackson et al. | 3/1.911 |
| 4,038,705 | 8/1977 | Owens et al. | 3/2 |
| 4,085,466 | 4/1978 | Goodfellow et al. | 3/1.91 |

FOREIGN PATENT DOCUMENTS 591845  9/1977  Switzerland ............................ 3/1.911

Primary Examiner—Clifford D. Crowder
Attorney, Agent, or Firm—Maurice R. Salada; James W. Wright

[57] ABSTRACT

A prosthesis for knees and other joints comprises two portions which are disposed side by side and which are at least partially spaced apart from one another. Each portion of the prosthesis includes a pair of spaced apart, relatively inextensible primary components. Disposed between and spaced from the primary components in each portion of the prosthesis is a pivot member. Each pivot member is resiliently secured to the two corresponding primary components of its portion of the prosthesis so as to permit and accommodate relative rotation between the pivot member and the primary components. As a result, the two primary components of each portion of the joint prosthesis can rotate toward and away from one another about an axis that is disposed at least adjacent to and at least approximately parallel to a central axis of the corresponding pivot member. The pivot member and the primary components of each portion of the prosthesis are preferably secured together by one or more bodies of elastomer.

5 Claims, 5 Drawing Figures

KNEE JOINT PROSTHESIS

RELATED APPLICATIONS

The present application describes, illustrates, and claims a joint prosthesis similar in structure and operation to joint prostheses described, illustrated, and claimed in a commonly owned, concurrently filed application Ser. No. 852,183 of Leonard J. Schwemmer, entitled "Joint Prosthesis", in a commonly owned, concurrently filed application Ser. No. 852,181 of James B. Koeneman, entitled "Joint Prosthesis With Contoured Pin", and in a commonly owned, concurrently filed joint application Ser. No. 852,182 of Leonard J. Schwemmer and Howard T. Wilson, entitled "Ankle Joint Prosthesis".

BACKGROUND OF THE INVENTION

Resilient materials, such as elastomers, have long been used in external prosthetic devices for the human body to cushion impact or shock loads. Because impact loads are necessarily and regularly encountered in walking, two common prosthetic devices that have often incorporated resilient materials are artificial feet and ankle joint prostheses for use with artificial feet. In early designs, an ankle joint prosthesis was typically a metallic pivot that included a plain (e.g., sleeve) bearing or a rolling element (e.g., ball) bearing. Resilient or elastomeric material was disposed both about the pivot to help limit its motion and in various portions of an associated artificial foot to cushion or absorb impact loads. Typical combinations of a cushioned artificial foot and an ankle joint prosthesis that incorporates a metal-on-metal pivot are described and illustrated in Ehle U.S. Pat. No. 487,697, Rowley U.S. Pat. No. 1,090,881, and Kaiser U.S. Pat. No. 2,183,076.

Later in the development of ankle joint prostheses for external use, resilient or elastomeric material came to be utilized in such prostheses for properties other than its ability to absorb or cushion impact loads. In Desoutter U.S. Pat. No. 1,911,440, for example, a tubular rubber bushing is secured between a pin and a metal sleeve that circumscribes the pin to form a pivot for an ankle joint prosthesis. The outer sleeve is connected to an artificial foot, while the pin is connected to an artificial lower leg. Articulation is permitted by torsional deflection of the bushing. Because of the resilience of the bushing material, the ankle joint prosthesis automatically returns to a preselected position after it is deflected. The joint also does not require lubrication because the bushing separates the adjacent metal surfaces of the pin and the sleeve. Similar ankle joint prostheses that employ a tubular bushing or body of elastomer between an outer rigid sleeve and an inner pin or sleeve are described and illustrated in Burger et al U.S. Pat. No. 2,605,475 and Prahl U.S. Pat. No. 3,480,972.

A pivot or pivotable assembly that incorporates a relatively thin, tubular body of elastomer secured between a pin and a larger diameter sleeve is only capable of extensive pivotal or rotational movement about a single axis. In typical ankle joint prostheses, including the Desoutter and Prahl ankle joint prostheses, such an elastomeric pivot is oriented generally perpendicular to the longitudinal axis of the wearer's leg and transverse to the longitudinal axis of the wearer's artificial foot. In the orientation that has been described, the elastomeric pivot permits extensive flexion in the dorsal and plantar directions. An elastomeric pivot so oriented, however, can only provide a limited degree of inversion and eversion of a foot about its longitudinal axis or a parallel axis and only a limited degree of internal and external rotation of the foot about the longitudinal axis of the lower leg. The motions other than flexion are all accommodated primarily through compression of the elastomeric bushing, which is relatively thin and cannot afford any significant degree of deflection. To overcome some of the motion limitations inherent in the ankle joint prostheses of the Desoutter and Prahl patents, the ankle joint prosthesis of the previously mentioned Burger et al patent incorporates two elastomeric pivots disposed at right angles to each other. The Burger et al ankle joint prosthesis thus can resiliently permit both extensive dorsal and plantar flexion and extensive inversion and eversion. Other external ankle joint prostheses attempt to provide the three types of movement afforded by a natural ankle joint through the use of relatively massive blocks of elastomer, rather than the tubular bushings discussed above. The blocks of elastomer may be specially shaped or contoured in order to provide appropriate stiffnesses or motion capabilities in the three critical rotational directions. Examples of external ankle joint prostheses that incorporate large blocks of elastomer are described and illustrated in Bennington et al U.S. Pat. No. 2,692,392 and Asbelle et al U.S. Pat. No. 3,982,280.

Although resilient materials, and particularly elastomeric materials, have for many years been suggested for use in external joint prostheses, the use of resilient or elastomeric materials in internal joint prostheses has only recently been proposed. The apparent delay in the appearance of proposals for the use of resilient or elastomeric materials internally of the human body is probably attributable in part to the lack of a physiologically inert elastomeric material that could safely be used in the body. Nonetheless, with the development of suitable elastomeric materials, such as Dow Corning Corporation's Silastic ® silicone elastomer, a number of surgically implantable, elastomeric joint prostheses have been proposed, particularly for finger joints. The finger joint prostheses, in particular, tend to be entirely formed of elastomer or nearly so. Unfortunately, such designs require the elastomer to be bent or flexed extensively at some point to provide a pivot. The result is alternating tension and compression loading of the elastomer, which is detrimental to its long-term fatigue life. The use of notches in the elastomer to locate the pivot point further adds to the stresses in the elastomer. Examples of finger joint prostheses that are entirely formed of elastomer or nearly so are described and illustrated in Swanson U.S. Pat. No. 3,462,765, Niebauer et al U.S. Pat. No. 3,593,342, Lynch U.S. Pat. No. 3,681,786, and Swanson U.S. Pat. No. 3,875,594. Other than the finger joint prostheses mentioned above, relatively few implantable prostheses that employ resilient or elastomeric material have been identified. Nonetheless, the use of elastomeric material in an implantable hip joint prosthesis is suggested in Buechel et al U.S. Pat. No. 3,916,451, particularly FIG. 1, and in Bokros et al U.S. Pat. No. 3,707,006, particularly FIG. 5. The use of elastomeric material in an implantable knee joint is suggested in Martinez U.S. Pat. No. 3,909,854.

The ankle joint prostheses described in the previously mentioned patents to Desoutter, Burger et al and Prahl appear to represent the best presently known designs for use of the desirable properties of elastomeric material in a prosthesis that accommodates pivotal or rotational motion. Nonetheless, the elastomeric pivots that are incorporated in the ankle joint prostheses of these three patents do not make optimal use of elastomeric material within the space provided. In particular, the relatively thin, tubular bodies of elastomer in the ankle joint prostheses of Desoutter, Burger et al, and Prahl are subject to relatively high, torsionally-induced strains which, over periods of extended use, will lead to failure of the elastomeric bodies. While the strains experienced by the elastomeric bodies of the patented ankle joint prostheses may not be detrimental in terms of a few hundred or even a few thousand articulations of the prostheses, the strains are critical when one considers several million articulations or deflections of the prostheses. Such numbers of articulations may easily be experienced during a year or two of normal use. In an ankle joint prosthesis that is used externally of the human body, replacement of the elastomeric elements of the prosthesis may merely represent additional expense and some inconvenience to the user. If such a joint prosthesis were implanted in the body of the user, on the other hand, failure of the elastomeric elements within one or two years would seriously limit the desirability of using such a prosthesis.

SUMMARY OF THE INVENTION

The present invention is directed to a joint prosthesis for internal or external use which is constructed to afford resilient accommodation of pivotal motion and which so incorporates resilient material as to obtain a maximum service life. The joint prosthesis of the invention structurally resembles the prostheses described and illustrated in a commonly owned, concurrently filed application of Leonard J. Schwemmer, entitled "Joint Prosthesis", but is specially configured for use in a knee or similar joint in which extensive pivotal motion about two mutually perpendicular axes is desirable. A prosthesis for knees and other joints according to the present invention comprises two joint portions which are disposed side by side and which are at least partially spaced apart from one another. Each portion of the prosthesis includes a pair of relatively inextensible components that are spaced apart. Disposed between and spaced from each of the primary components in each portion of the prosthesis is a relatively inextensible pivot member. Each pivot member is resiliently secured to each of the two primary components of its portion of the prosthesis so as to permit and accommodate relative rotation between the pivot member and each of the primary components. As a result, the two primary components of each portion of the prosthesis can rotate toward and away from one another about an axis that is disposed at least adjacent to and at least approximately parallel to a central axis of the corresponding pivot member.

In some embodiments of the invention, corresponding primary components of the two portions of the prosthesis may be portions of a single structural member. Likewise, the pivot members of the two portions of the prosthesis may simply be portions of a single pivot member. In a preferred embodiment of the invention, however, the pivot members, at least, of the two portions of the joint prosthesis are discrete elements that are spaced apart from each other. The use of two discrete and spaced apart pivot members permits the prosthesis to have a high resistance to side-to-side pivotal movements, while accommodating extensive pivotal motion about two other axes that are generally perpendicular to one another. Thus, for example, in a knee, it is desirable to have extensive pivotal motion between an associated tibia and femur both as flexion about an axis which is disposed generally normal to the longitudinal axes of both bones and which extends from side to side of the knee and as rotation about an axis roughly parallel to or coincident with the longitudinal axis of at least one of the two bones. At the same time, it is desirable to avoid extensive adduction and abduction or pivotal motions about an axis that is generally normal to the longitudinal axes of the femur and tibia and extends from front to rear of the knee. In the preferred embodiment of the invention, flexion, or pivotal movement associated with bending a knee, is provided by relative pivotal motion or rotation between the two primary components of each portion of the prosthesis about an axis which is approximately coincident with a central axis of the corresponding pivot member and which extends from one portion of the prosthesis to the other. Rotation, or relative twisting motion of a tibia and femur about the longitudinal axis of one or the other of the bones, is provided by pivotal motion between the two primary components of each portion of the prosthesis about a vertical axis that passes between the two prosthesis portions and by rolling motions of the two pivot members. The rolling motions of the two pivot members occur in different rotational directions about their respective central axes. Adduction and abduction between the tibia and femur are limited by virtue of the spacing between the two portions of the joint prosthesis, among other reasons.

The structure that secures the pivot member to the primary components of each portion of the prosthesis of the invention is preferably at least partially formed of elastomer. The securing structure of each portion of the prosthesis also preferably includes two distinct resilient portions, each of which secures the pivot member to a different one of the two primary components. In each portion of the resilient securing structure, a pair of exposed surfaces extend generally lengthwise of the pivot member and outwardly from adjacent the pivot member. The exposed surfaces of the two portions of the securing structure in each portion of the prosthesis are spaced apart throughout at least a majority of their respective lengths measured generally radially of the central axis of the pivot member. As a result of the spacing between the exposed surfaces, deflection of one portion of the securing structure to accommodate relative pivotal motion or rotation between the pivot member and one of the primary components of either portion of the prosthesis does not interfere with deflection of the other portion of the securing structure to accommodate relative rotation between the pivot member and the other primary component of that portion of the prosthesis. To facilitate pivotal movements, each of the primary components of the prosthesis should include a surface that is concavely arcuate in shape when viewed in section taken generally normal to the central axis of the pivot member. The arcuate surfaces of the primary components in each portion of the prosthesis are presented to a convexly arcuate surface or surfaces of the corresponding pivot member.

BRIEF DESCRIPTION OF THE DRAWING

For a better understanding of the invention, reference may be made to the following description of several examplary embodiments, taken in conjunction with the figures of the accompanying drawing in which.

DESCRIPTION OF EMBODIMENTS

Figure 1:
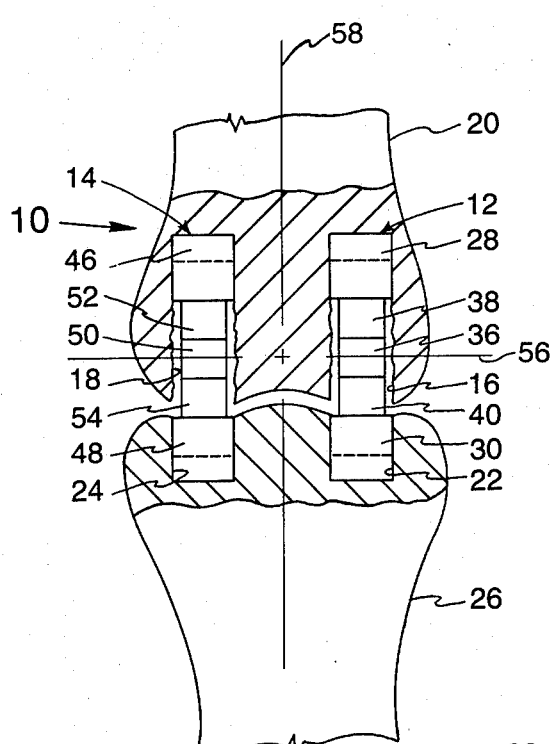
FIG. 1 is a front view of a joint prosthesis according to the invention when implanted in a human body to replace a knee joint.
Figure 2:
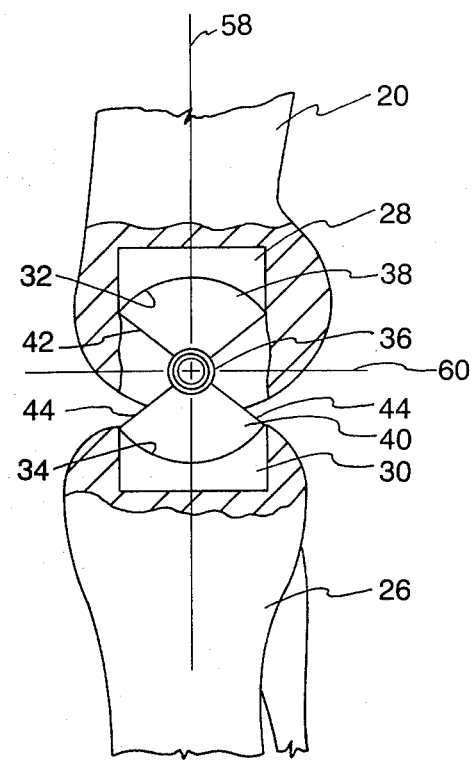
FIG. 2 is a side view of the joint prosthesis of FIG. 1.

FIG. 1 of the drawing illustrates, in frontal view, a knee joint prosthesis 10, according to the present invention, which includes two separate and distinct joint portions 12 and 14. As illustrated in FIGS. 1 and 2, each of the two portions 12 and 14 of the prosthesis 10 is implanted at one end in a groove 16 or 18 that is surgically formed in a condyle of a femur 20. The other end of each portion 12 or 14 of the prosthesis 10 is similarly implanted in a surgically formed groove 22 or 24 in the plateau of an adjacent tibia 26. The grooves 16 and 18 in the femoral condyles are significantly deeper than the grooves 22 and 24 formed in the tibial plateau. The total depth of the two grooves that receive each portion 12 or 14 of the prosthesis 10 is such that there is substantially no overall lengthening of the leg in which the prosthesis is implanted.

The two portions 12 and 14 of the prosthesis 10 are identical to each other. The right-hand portion 12, as viewed in FIG. 1, includes a femoral component 28 and a tibial component 30 that is spaced apart from the femoral component. Each of the components 28 and 30 is formed of a material which is relatively inextensible and which may be safely implanted in the human body. Suitable materials include high density polyethylene, polyester, nylon, silicone resins, stainless steel, cobalt-chromium alloys, titanium, and titanium alloys. The materials are to be judged as to their relative inextensibility through comparison to the resilient materials used in the prosthesis 10, which are described below. Each of the components 28 and 30 is a generally rectangular solid with one surface 32 or 34 that is concavely arcuate in shape. In the illustrated embodiment of the prosthesis 10, the surfaces 32 and 34 are curved only in a single direction or only in planes generally parallel to the plane of FIG. 2 of the drawing. Nonetheless, the surfaces 32 and 34 might also be curved in a direction into the plane of the drawing or, in other words, in planes perpendicular to the plane of the drawing in order to provide additional motion accommodation in a manner that will become apparent. The nonarcuate surfaces of the femoral and tibial components 28 and 30 of the portion 12 of the prosthesis 10 are secured to adjacent surfaces of the boney tissue in which the components are implanted. The attachment to the boney tissue will typically be accomplished through the use of bone cement, such as a self-curing polymethylmethacrylate cement. The surfaces of the components 28 and 30 other than the arcuate surfaces 32 and 34 may be fluted or otherwise contoured to facilitate or improve the mechanical connection between the components and the cement. Application of a porous coating to the components 28 and 30 will promote ingrowth of the boney tissue into the nonarcuate surfaces of the components and improve the attachment between the prosthesis 10 and the boney tissue of the femur 20 and the tibia 26.

Disposed between the femoral and tibial components 28 and 30 of the right-hand portion of the prosthesis 10 and, more particularly, between the arcuate surfaces 32 and 34 of the two components is a relatively short, cylindrical pin or pivot member 36. The pin 36 is formed of a relatively inextensible material, such as any one of the materials previously suggested for use in the primary components 28 and 30 of the right-hand portion 12 of the prosthesis 10. As can be seen in FIG. 2, the convexly arcuate outer circumference of the pin 36 is presented to the concavely arcuate surfaces 32 and 34 of the components 28 and 30. The pin 36 is secured to the femoral and tibial components 28 and 30 by a pair of arcuately shaped bodies 38 and 40 of a resilient material, such as a biocompatible elastomer. Each of the resilient bodies 38 and 40 resembles a wedge-shaped section from an annulus. The resilient body 38 is bonded, such as by adhesives, to the outer circumference of the pin 36 and extends between the pin and the concavely arcuate surface 32 of the femoral component 28. The resilient body 38 is also bonded to the arcuate surface 32. In a similar manner, the resilient body 40, which is disposed opposite the resilient body 38 relative to the pin 36, extends between the pin and the tibial component 30. The resilient body 40 is bonded to the convexly arcuate outer surface of the pin 36 and to the concavely arcuate surface 34 of the tibial component 30.

The resilient body 38 includes a pair of exposed surfaces 42 that extend generally lengthwise of the pin 36 and outwardly from adjacent the pin in a generally radial direction. Similarly, the resilient body 40 includes a pair of exposed surfaces 44 that also extend generally lengthwise of the pin 36 and generally radially outwardly from adjacent the pin. The exposed surfaces 42 of the resilient body 38 are spaced from the exposed surfaces 44 of the body 40 throughout at least a majority of their respective lengths measured generally radially of the pin. In the illustrated embodiment of the invention, the surfaces 42 are totally separate from the surfaces 44. It would be possible, however, for the two pairs of surfaces 42 and 44 to meet at or near the pin 36 to form an apex for the angle between them. Because the surfaces 42 of the resilient body 38 are spaced from the surfaces 44 of the resilient body 40, the resilient body 38, for example, is free to deflect in shear to accommodate motion between the primary components 28 and 30 of the prosthesis 10 without interferring with similar deflection of the resilient body 40. Although the resilient body 38 is depicted as totally separate from the resilient body 40, the two resilient bodies might actually be joined by a relatively thin skin of elastomer extending around the outer circumference of the pin 36, as suggested in FIG. 3, or merely be portions of a continuous resilient annulus.

As previously stated, the left-hand portion 14 of the joint prosthesis 10 is identical to the right-hand portion 12 in configuration and construction. It may be desirable, however, for the prosthesis portion 14 to have a different configuration or size depending upon circumstances such as whether the portion 14 is to be placed in the medial or in the distal condyle of the femur 20. Typically, the medial condyle of a femur carries greater loads than the distal condyle. Thus, the portion of the prosthesis 10 which is implanted in the medial condyle might have to be more massive, for example, than the portion implanted in the distal condyle. The prosthesis portion 14 includes a femoral component 46 and a tibial component 48, both of which are formed of relatively inextensible and biocompatible material. The femoral and tibial components 46 and 48 are spaced apart from one another and disposed between them is a relatively short, cylindrical pin or pivot member 50 that is also formed of relatively inextensible material. The materials of which the two components 46 and 48 and the pin 50 may be formed are the same as the materials from which the corresponding elements of the other portion 12 of the prosthesis 10 may be formed. Disposed between the pin 50 and the two primary components 46 and 48 of the left-hand portion 14 of the prosthesis 10 are two bodies of resilient material 52 and 54. The resilient bodies 52 and 54 are identical in shape to the corresponding resilient bodies 38 and 40 of the right-hand portion 12 of the prosthesis 10 and may be formed of the same materials, such as a biocompatible elastomer. The resilient body 52 extends between the convexly arcuate outer circumference of the pin 50 to a corresponding, but concavely arcuate surface (not shown) of the femoral component 46. The resilient body 52 is bonded to both arcuate surfaces. Similarly, the resilient body 54 is bonded to the convexly arcuate outer surface of the pin 50 and extends from the pin to the tibial component 48. The resilient body 54 is bonded to a concavely arcuate surface (not shown) of the tibial component 48.

In operation, when implanted in a human body, the joint prosthesis 10 functions both to carry the load represented by the weight of the body supported by the leg in which the joint is implanted and to facilitate pivotal or rotational movement about two axes 56 and 58 which are generally perpendicular to one another. The weight of the body of the user of the prosthesis 10 is transmitted from the femur 20 into the femoral components 28 and 46 of the prosthesis. From the femoral components 28 and 46, the weight is transferred through the resilient bodies 38 and 40 and 52 and 54 and the pins 36 and 50 of the portions 12 and 14, respectively, of the prosthesis 10 into the tibial components 30 and 48 of the prosthesis. The weight is then transmitted from the tibial components 30 and 48 into the tibia 26. The relatively inextensible elements of the prosthesis, such as the primary components 28, 30, 46 and 48 and the pins 36 and 50, rigidly carry their applied loads, which will be well within their strength capabilities. The resilient elements 38, 40, 52 and 54 carry their applied loads in compression with some bulging or deflection of the resilient material in lateral directions. Since elastomeric materials, for example, are relatively strong when loaded in compression, the resilient elements 38, 40, 52 and 54 are also able to accommodate and carry the weight of the user's body without failure or other difficulty. The resilience of the bodies 38, 40, 52 and 54 provides some shock absorption capabilities so that impact loads are not transmitted directly to other portions of the user's body.

Pivotal movements between the femur 20 and the tibia 26 are accommodated through deflection of the resilient elements 38, 40, 52, and 54. Flexion, or bending of the knee about the axis 56 which is generally coincident with the central longitudinal axes of the two pins 36 and 50, requires relative pivotal motion or rotation between the components 28, 30, 46 and 48 of the two portions 12 and 14 of the prosthesis 10 and their respective pins 36 and 50. The relative rotation is accommodated by deflection of the resilient bodies 38, 40, 52, and 54 in torsional shear about the axis 56. The spacing between the components 28 and 30 and the components 46 and 48, together with the spacing between the exposed surfaces 42 and 44, for example, insures relatively free pivotal motion between the components 28, 30, 46, and 48 and their respective pins 36 and 50 through relatively large angles of rotation. Some restraint on the pivotal motion will result from the resilience of the resilient bodies 38, 40, 52, and 54, which tends to return the primary components 28, 30, 46, and 48 to their starting orientations. Nonetheless, the primary restraint or control on motions of the prosthesis 10 when implanted in the body will normally be provided by the user's ligaments and muscles, which will be left intact to the extent possible.

Rotation between the femur 20 and the tibia 26 or, viewed another way, relative pivotal motion between the femur and the tibia about an axis 58 that is roughly parallel to the longitudinal axis of at least one of the two bones and generally perpendicular to the axis 56, requires relative pivotal motion between the femoral components 28 and 46 of the prosthesis 10, on the one hand, and the tibial components 30 and 48 of the prosthesis, on the other hand. To better describe the various movements that actually occur between the elements of the prosthesis 10, it will be assumed, as an example, that the femur 20 is to rotate with respect to the tibia 26 about the axis 58 in a direction such that the front or left-hand portion of the femur, as viewed in FIG. 2, turns into the plane of the drawing, while the rear or right-hand portion of the femur 20 moves out of the plane of the drawing toward the viewer. The femoral components 28 and 46 of the prosthesis 10 will thus pivot or twist relative to the tibial components 30 and 48 about the axis 58. To complement the pivotal motion between the components 28 and 46 and the components 30 and 48, one might expect that the pins 36 and 50 would merely pivot about axes which are parallel to the axis 58 but which pass through the centers of the pins. In fact, however, the pin 36 tends not only to pivot about a vertical axis as a result of the urging of the resilient body 38, but also to rotate about an axis corresponding to the axis 56 and to roll to the left, as viewed in FIG. 2. Similarly, the pin 50, which is disposed immediately behind the pin 36 as viewed in FIG. 2, will tend not only to twist about a vertical axis but also to rotate about an axis corresponding to the axis 56 and to roll to the right as viewed in FIG. 2. The combined rolling and twisting motions of the pins 36 and 50, which is facilitated by the separation between the two portions 12 and 14 of the prosthesis 10, particularly the separation between the pins 36 and 50, contribute to an acceptably low torsional spring rate for the prosthesis 10 with respect to pivotal motion about the axis 58.

Abduction and adduction, which are relative pivotal motions between the femur 20 and the tibia 26 about an axis 60 which lies in a plane that is normal to the longitudinal axis of at least one of the bones and which passes from front to rear between the two portions 12 and 14 of the prosthesis 10, requires tilting between the femoral components 28 and 46, on one hand, and the tibial components 30 and 48, on the other hand, to the left and/or to the right, as viewed in FIG. 1. Such tilting motions are accommodated by bending or flexing of the resilient bodies 38, 40, 52, and 54, which is a combination of compression loading of one side of each resilient body and tension loading of the other side of the resilient body.

Because of the separation between the two portions 12 and 14 of the prosthesis 10, the prosthesis effectively supports the femur 20 at two points, rather than just one, and thus appears relatively rigid or inflexible in response to abduction and adduction. The necessity of deflecting the elastomer of the prosthesis 10 in compression also makes abduction and adduction more difficult. Another limitation on such motion is the available clearance between the various elements of the two portions 12 and 14 of the prosthesis 10, on the one hand, and the side walls of the grooves 16 and 18, on the other hand. Contact between the femur 20 and either the tibia 26 or the tibial components 30 and 48 of the prosthesis 10 may also limit abduction and adduction.

Figure 3:
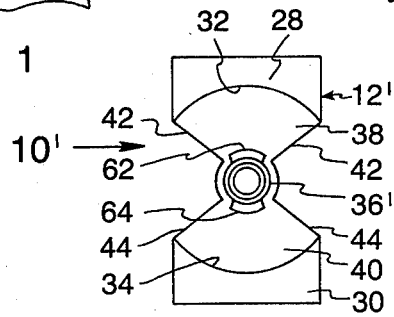
FIG. 3 is a view corresponding to the view shown in FIG. 2, but illustrating a different configuration for the pivot member of the prosthesis.

FIG. 3 of the drawing illustrates an alternate embodiment 10' of the invention. In FIG. 3, elements of the prosthesis 10' which correspond to elements of the prosthesis 10 are designated with corresponding reference numerals. Elements that have different configurations from their counterparts in FIGS. 1 and 2 are designated with corresponding, but prime reference numerals. The illustrated portion 12' of the joint prosthesis 10' includes a pin 36' that has a configuration which differs from the configuration of the pin 36 shown in FIGS. 1 and 2. When viewed in a plane normal to its central longitudinal axis, the pin 36' does not have a continuous, circular outer circumference, but instead has two discrete, arcuate surfaces 62 and 64 disposed opposite each other about the circumference of the pin. The remainder of the circumference of the pin 36' between and on each side of the two arcuate surfaces 62 and 64 is generally of a smaller diameter than the portions of the circumference defined by the surfaces 62 and 64. The resilient body 38 extends between and is bonded to the arcuate surface 32 of the femoral component 28 and the adjacent arcuate surface 62 of the pin 36'. In a similar manner, the resilient body 40 extends between and is bonded to the arcuate surface 34 of the tibial component 30 and the arcuate surface 64 of the pin 36'. Adjacent the two surfaces 62 and 64 of the pin 36', the resilient bodies 38 and 40 have circumferential dimensions that are greater than the corresponding dimensions of the surfaces 62 and 64. Consequently, the exposed surfaces 42 and 44 of the resilient bodies 38 and 40, respectively, extend to the smaller diameter portions of the circumference of the pin 36' and do not stop at the arcuate surfaces 62 and 64. As is explained in a commonly owned, concurrently filed application of James B. Koeneman, entitled "Joint Prosthesis With Contoured Pin", the special contour of the circumference of the pin 36' provides stress relief at the interfaces between the resilient bodies 38 and 40 and the pin 36'.

Figure 4:
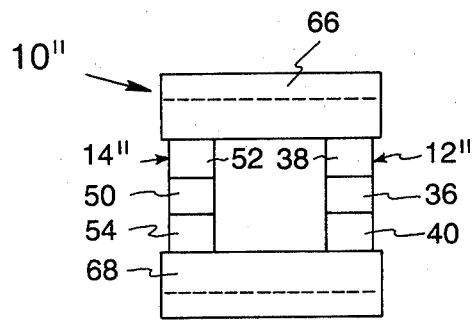
FIG. 4 is a view corresponding to the view shown in FIG. 1 of another embodiment of the joint prosthesis of the invention.

In FIG. 4 of the drawing, there is illustrated another embodiment 10" of the invention in which the femoral components of the two portions 12" and 14" of the prosthesis are merely different portions of a single member 66. Similarly, the tibial components of the two portions 12" and 14" of the prosthesis 10" are merely different portions of a single component or element 68. As in FIG. 3, elements of the prosthesis 10" that correspond to elements of the prosthesis 10 of FIGS. 1 and 2 are designated with the same reference numerals, double primed reference numerals being utilized to designate similar components that have modified structures. The prosthesis 10" eliminates the necessity for making two separate grooves 16 and 18 and 22 and 24 in the femoral condyles and the tibial plateau, respectively, to receive the primary components of the prosthesis 10". On the other hand, implantation of the prosthesis 10" will also require the removal of substantial boney tissue that might otherwise be usefully employed to secure the prosthesis 10" to the bones in which the prosthesis is implanted. The prosthesis 10" may be a desirable embodiment for use externally of the human body, inasmuch as the two portions 12" and 14" of the prosthesis are conveniently joined together in an integral unit without adverse effect on their function, as described above with reference to the prosthesis 10.

Figure 5:
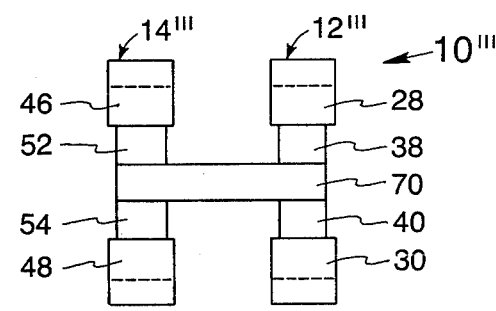
FIG. 5 is also a view corresponding to the view shown in FIG. 1 of yet another embodiment of a joint prosthesis according to the invention.

FIG. 5 of the drawing illustrates yet another embodiment 10''' of the invention in which the two portions 12''' and 14''' of the prosthesis share a common pin 70. As with the embodiments of the invention shown in FIGS. 3 and 4, the elements of the prosthesis 10''' which correspond to elements of the prosthesis 10 shown in FIGS. 1 and 2 are designated with the same reference numerals. Corresponding elements that have modified structures are designated with similar, but triple primed reference numerals, where appropriate. The use of a common pin 70 linking the two otherwise separate portions 12''' and 14''' of the prosthesis 10''' will result in a higher rotational spring rate or resistance to rotation of the prosthesis 10''' with respect to pivotal motion between a femur and a tibia about an axis corresponding to the axis 58 in FIGS. 1 and 2. The increased rotational stiffness results from the restraint imposed by the common pin 70 on the previously described, independent rolling motion that would result if two separate pins were used. The desirability of using a single pin 70 will depend upon the particular characteristics desired of a knee joint prosthesis.

Although the foregoing embodiments of the present invention have all been described and illustrated with resilient bodies that are formed entirely of elastomer, the resilient bodies may incorporate thin plates or shims of relatively nonextensible material disposed parallel to and spaced apart from one another within the resilient bodies. The addition of inextensible shims will limit the ability of the resilient bodies, particularly if they are formed of elastomer, to bulge or deflect laterally in response to compressive loads. The limitation on bulging effectively increases the ability of the resilient bodies to carry compressive loads and decreases their vertical deflections, for example, in response to any given vertical load. By contouring such inextensible shims to match the contours of the surfaces between which and to which the resilient bodies are bonded (e.g., arcuate surfaces 32 and 34), the shims will not interfere with pivotal motions because the resilient bodies will be free to deflect in shear between the nonextensible shims embedded in each resilient body. The shims may be fabricated of any biocompatible material, such as the materials of which the primary components 28, 30, 46, and 48 and the pins 36 and 50 of the prosthesis 10 may be formed. As with the other relatively inextensible elements used in the prosthesis 10, for example, shims are to be judged relatively inextensible in comparison to the material utilized in the resilient bodies 38, 40, 52 and 54.

The term "pin" is used throughout the foregoing descriptions to designate a relatively inextensible member about which the primary components of each prosthesis pivot. The illustrated pins include both a relatively long, slender cylindrical member, such as the member 70 shown in FIG. 5, and a relatively short, cylindrical member, such as the pin 36 of FIG. 1. Nonetheless, the term "pin" is intended to include members that are not cylindrical. In particular, it would be possible and, in some cases desirable, to form a pin with a curvature along its length so as to be spherical, for example, or approximately spherical in overall configuration. The provision of an arcuate profile along the length of a pin will facilitate tilting motions, for example, such as relative pivotal motion between the femur 20 and the tibia 26, as shown in FIGS. 1 and 2 of the drawing, about an axis such as the axis 60. Other possible pin shapes would include pins that are generally frustroconical.

It will be understood that the embodiments described above are merely exemplary and that persons skilled in the art may make many variations and modifications without departing from the spirit and scope of the invention. In addition, although all the foregoing embodiments are for use within the human body, it is intended that similarly constructed joint prostheses could be used externally of the human body between an artificial upper leg and artificial lower leg, for example. All such modifications and variations are intended to be within the scope of the invention as defined in the appended claims.

What is claimed is:

1. A joint prosthesis for use in replacement of a skeletal knee joint which joint permits movement of adjacent body members in flexion about a flexion axis and in rotation relative to each other about an axis extending longitudinally through at least one of the body members perpendicular to said flexion axis, comprising:
   first joint component means for connection with one body member, and second joint component means for connection with said adjacent body member;
   first and second pivot members, said first and second pivot members being spaced apart on opposite sides of said longitudinal axis and disposed between said first and second joint component means; and
   securing means including a pair of first bodies of elastomeric material and a pair of second bodies of elastomeric material, said pair of first bodies of elastomeric material being disposed between and attaching to said first joint component means and respective ones of said pivot members, said pair of second bodies of elastomeric material being disposed between and attaching to said second joint component means and respective ones of said pivot members, said first pair of bodies of elastomeric material and said second pair of bodies of elastomeric material being spaced apart and suspending said pivot members between said first and second joint component means to permit motion of said first and second joint component means relative to each other about said flexion axis in response to flexion movement of said adjacent body members, said pivot members pivoting about axes parallel to said longitudinal axis and independently rotating in opposite directions about axes in a plane normal to said longitudinal axis in response to rotational movement of said adjacent body members relative to each other, said pivot members cooperating with said first and second bodies of elastomeric material in simulating the operation of a knee joint in the human body.

2. The joint prosthesis of claim 1 wherein said first and second joint component means each include a single section of biocompatible inextensible material.

3. The joint prosthesis of claim 1 wherein said first and second joint component means each include two separate and spaced apart sections of biocompatible inextensible material.

4. The joint prosthesis of claim 1 wherein said first joint component means is formed for attachment to a condyle of a femur in the human body.

5. The joint prosthesis of claim 1 wherein said second joint component means is formed for attachment to the plateau of a tibea in the human body.

* * * * *